United States Patent
Asikkala et al.

(10) Patent No.: US 9,187,444 B2
(45) Date of Patent: Nov. 17, 2015

(54) PROCESS FOR CONVERTING BIO-OIL

(71) Applicant: UPM-Kymmene Corporation, Helsinki (FI)

(72) Inventors: Janne Asikkala, Lappeenranta (FI); Andrea Gutierrez, Lappeenranta (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 14/202,372

(22) Filed: Mar. 10, 2014

(65) Prior Publication Data
US 2014/0256965 A1    Sep. 11, 2014

(30) Foreign Application Priority Data
Mar. 8, 2013   (FI) .................................. 20135223

(51) Int. Cl.
C07C 67/00 (2006.01)
C07D 307/42 (2006.01)
C07C 27/00 (2006.01)
C10L 1/02 (2006.01)

(52) U.S. Cl.
CPC .............. *C07D 307/42* (2013.01); *C07C 27/00* (2013.01); *C10L 1/02* (2013.01)

(58) Field of Classification Search
USPC ........................................ 568/312, 314, 402
See application file for complete search history.

(56) References Cited

U.S. PATENT DOCUMENTS

| | | |
|---|---|---|
| 2011/0139602 A1 | 6/2011 | Lin et al. |
| 2011/0146140 A1 | 6/2011 | Brandvold et al. |
| 2011/0296745 A1* | 12/2011 | Hilten et al. .................... 44/388 |
| 2012/0017494 A1 | 1/2012 | Traynor et al. |
| 2012/0035404 A1 | 2/2012 | Alegria et al. |

FOREIGN PATENT DOCUMENTS

| | | |
|---|---|---|
| CN | 102643687 A | 8/2012 |
| EP | 0718392 A1 | 6/1996 |
| WO | 2010099058 A2 | 9/2010 |
| WO | 2012018518 A2 | 2/2012 |
| WO | 2012061005 A2 | 5/2012 |

OTHER PUBLICATIONS

Zhang et al., "Upgrading Bio-oil over Different Solid Catalysts", Energy & Fuels, 2006, vol. 20, pp. 2717-2720.
Xu et al., "A novel method of upgrading bio-oil by reactive rectification", Journal of Fuel Chemistry and Technology, 2008, vol. 36, Issue 4, pp. 421-425.
Extended European Search Report, dated Aug. 1, 2014, from corresponding EP application.
Moens et al., "Study of the Neutralization and Stabilization of a Mixed Hardwood Bio-Oil", Energy & Fuel, vol. 23, pp. 2695-2699.
Finnish Search Report, dated Nov. 4, 2013, from corresponding FI application.

* cited by examiner

*Primary Examiner* — Sudhakar Katakam
*Assistant Examiner* — Pancham Bakshi
(74) *Attorney, Agent, or Firm* — Young & Thompson

(57) ABSTRACT

Disclosed is a process for converting bio-oil, wherein the process includes the steps, where a feedstock including bio-oil selected from bio-oils, any fractions of bio-oils and any combinations thereof is subjected to azeotropic distillation with at least one alcohol to yield a liquid component, and subjecting the liquid component to alcoholysis whereby converted bio-oil is obtained. The invention also relates to the use of converted bio-oil, obtainable by the process, as heating oil, as starting material in processes for producing fuels, fuel components, fine chemicals, chemical building-blocks, and solvents.

19 Claims, 1 Drawing Sheet

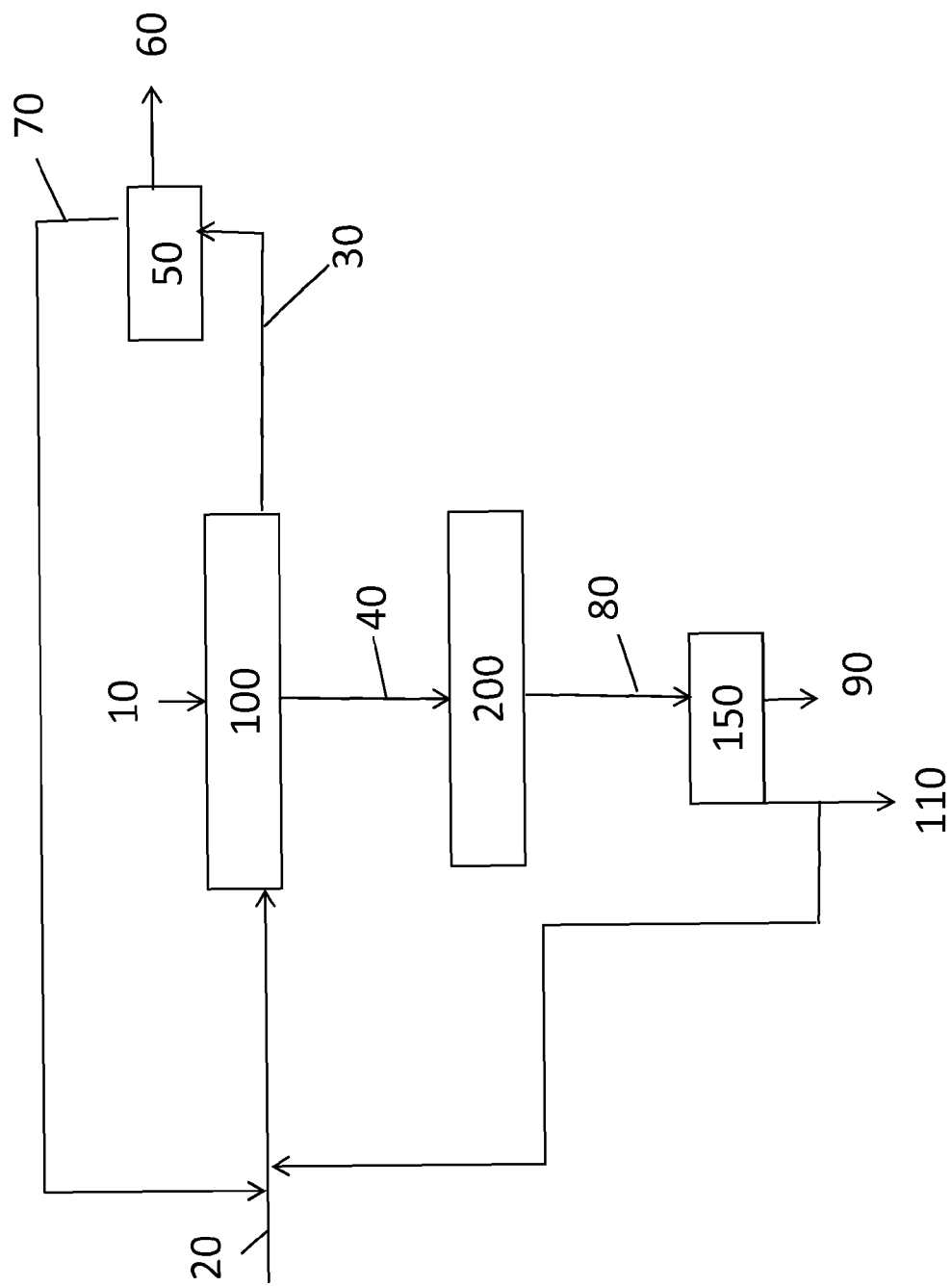

PROCESS FOR CONVERTING BIO-OIL

FIELD OF THE INVENTION

The present invention relates to converting of bio-oil, whereby the composition of bio-oil is altered, acidity is decreased and stability of bio-oil is improved. The invention also relates to subjecting bio-oil to azeotropic distillation with at least one alcohol, followed by alcoholysis to obtain converted bio-oil. The invention also relates to converted bio-oils obtainable by said process.

BACKGROUND OF THE INVENTION

Bio-oils of varying properties and compositions are obtained using numerous methods and processes. Bio-oils may be obtained for example from biomass using any suitable thermal treatment, pyrolysis and the like.

Pyrolysis is generally understood as the chemical decomposition of organic materials by heating in the absence or with limited supply of oxidizing agent such as air or oxygen. Pyrolysis can be used for converting biomass to pyrolysis oil which is an example of bio-oil. Commercial pyrolysis applications are typically either focused on the production of charcoal (slow pyrolysis) or production of liquid products (fast pyrolysis), the pyrolysis oil. Both the slow pyrolysis and the fast pyrolysis processes may be used for the manufacture of pyrolysis oil.

During pyrolysis of biomass, for example of lignocellulosic material, carried out at temperatures in the range 400-700° C., most of the cellulose and hemicellulose and part of lignin typically disintegrate to form smaller and lighter molecules which are vapors at the pyrolysis temperatures. During cooling some of the vapors condense forming a liquid product, called pyrolysis oil.

Bio-oils are complex mixtures of chemical compounds, including reactive aldehydes and ketones. Said reactive compounds react with each other whereby complex molecules having higher molecular weight are formed and the viscosity of bio-oil is increased. For example biomass derived pyrolysis oil typically comprises water, light volatiles and nonvolatiles. Further, pyrolysis oil has high acidity, which typically leads to corrosion problems, substantial water content, and high oxygen content.

Wood-based pyrolysis oil is the product of pyrolysis of wood or forest residues and it contains typically carboxylic acids, aldehydes, ketones, carbohydrates, thermally degraded lignin, water, and alkali metals. The oxygen-containing compounds (typically 40-50 wt-%) and water (typically 15-30 wt-%) make pyrolysis oils chemically and physically unstable. Although pyrolysis oils have higher energy density than wood, they are acidic (pH~2) and incompatible with conventional fuels. Furthermore pyrolysis oils have high viscosity and high solid content. Poor stability and high acidity are one of the key problems in utilizing the pyrolysis oil or storing for longer periods.

Due to its instability bio-oil is rapidly transformed to semisolid and gradually solid material, which is difficult to store or use for any further purposes. Thus, according to present practice it is necessary to process the bio-oils rapidly further in order to avoid the problems relating to stability.

Refining of bio-oils and particularly pyrolysis oil to provide fuel or fuel components is often very challenging due to the complex mixture of components of said bio-oil. For example pyrolysis oil typically consists of more than 200 identified compounds, which require very different conditions for converting them further to fuel components or precursors to fuel. Often this is carried out by hydroprocessing said pyrolysis oil over a hydrogenation catalyst in the presence of hydrogen. Since pyrolysis oil typically contains up to 50 wt % of oxygen, complete removal oxygen requires a substantial amount of hydrogen, even up to 1000 L/kg pyrolysis oil. The obtained light components are turned into gaseous products (hydrogen, methane, ethane, etc.) and heavy components are turned into coke and heavy oil. The heavy oil mixture needs further refinement to produce fuel fractions and this procedure requires high amounts of hydrogen and typically various different catalysts for obtaining the desired products.

CN 102643687 A suggests adding methanol in an amount from 1 to 21 wt % to bio-oils for improving stability, whereby viscosity can be reduced and the increase of water content in pyrolysis oil can be prevented.

WO 2012/061005 A2 teaches a process for converting pyrolysis oil to hydrocarbon fuels where pyrolysis oil is contacted with a feed comprising one or more alcohol species in a reactor to form an alcoholysis product, and contacting said alkoholysis product with a hydrotreating catalyst in the presence of hydrogen.

WO 2010/099058 A2 relates to a process for modifying the content of pyrolysis oil where pyrolysis oil vapor is treated with an atomized alcohol or amine under conditions allowing condensation between the carbonyl containing component and the alcohol or amine, and condensing the pyrolysis oil vapor and reaction product to form a pyrolysis oil product having an increased ester or amide content.

Despite the ongoing research and development relating to bio-oils, there is still a need to provide improved processes and methods for converting bio-oils to more valuable components in an efficient and economical way.

SUMMARY OF THE INVENTION

The present invention relates a process for converting bio-oil, whereby the composition of the bio-oil is altered, acidity is decreased and stability of said bio-oil is improved. Particularly the present invention relates to a process for converting bio-oil, where feedstock comprising bio-oil is subjected to azeotropic distillation with at least one alcohol to obtain a liquid component, and subjecting the liquid component to alcoholysis to form converted bio-oil i.e. an alcoholysis product. In the process converted bio-oil, having improved stability and less complicated composition comprising esters and acetals may be obtained.

The present invention also provides converted bio-oil, which may be used as such as heating oil and as starting material in processes for producing fuels, fuel components, fine chemicals and chemical building-blocks for chemical production and solvents.

The process for converting bio-oil comprises the steps where a feedstock comprising bio-oil is subjected to azeotropic distillation with at least one alcohol, and to alcoholysis, under conditions suitable for simultaneous esterification and acetal formation to obtain converted bio-oil.

Thus an object of the invention is to provide a process for effectively and economically converting bio-oil, whereby the composition of said bio-oil is altered, viscosity is decreased and stability improved.

Another object of the invention is to provide converted bio-oil, suitable for use as such or in the manufacture of more valuable components, particularly fuels and fuel components.

Still another object of the invention is to provide converted bio-oils based at least partly or totally on renewable starting materials for use as such or in the manufacture of more valuable components.

DEFINITIONS

The term "alcoholysis" refers here to the replacement of a carbon-oxygen bond in carbonyl compound by the addition of alcohol. An example of alcoholysis is the general chemical reaction involving an ester formation between carboxylic acid and alcohol, another example is the reaction of a carbonyl compound with an alcohol to form acetal.

The term "hydroprocessing" refers here to catalytic processing of organic material by all means of molecular hydrogen.

The term "carbonyl compounds" refers here to all organic molecules containing one or more carbonyl groups, such as aldehydes and ketones.

The term "chemical building-blocks" or "building-block chemicals" refer to chemical compounds useful as starting materials and intermediates for the manufacture of chemical and pharmaceutical final products. Examples of such chemical building-blocks are fumaric acid, furfural, glycerol, citric acid, treonin, propanic acid etc.

Transportation fuels refer to fractions or cuts or blends of hydrocarbons having distillation curves standardized for fuels, such as for diesel fuel (middle distillate from 160 to 380° C., EN 590), gasoline (150-210° C., EN 228), aviation fuel (160 to 300° C., ASTM D-1655 jet fuel), kerosene, naphtha, etc.

BRIEF DESCRIPTION OF THE DRAWINGS

FIG. 1 is a schematic flow diagram representing one embodiment of the process for converting bio-oils.

DETAILED DESCRIPTION OF THE INVENTION

It was surprisingly found that a feedstock comprising bio-oils can be converted in an efficient manner to more valuable products, with a process where a feedstock comprising bio-oil is subjected to azeotropic distillation with at least one alcohol (i.e. alcohol feedstock), to obtain a liquid component, and subjecting the liquid component to alcoholysis to form converted bio-oil. In said process the feedstock comprising bio-oil is subjected to azeotropic distillation with at least one alcohol under conditions suitable for enacting said azeotropic distillation where water is removed, followed by alcoholysis under conditions suitable for obtaining alcoholysis product comprising esters and acetals, and to obtain converted bio-oil.

The azeotropic distillation step will remove water from the bio-oil and the alcoholysis step will produce more stable and homogenous product from the bio-oil and increase the chain length of compounds contained therein.

The converted bio-oil may be used as starting material or feedstock in further refinement steps, such as hydroprocessing, where the hydrogen consumption may be decreased significantly and more valuable long chain hydrocarbons may be obtained, said long chain hydrocarbons being particularly suitable as fuels or fuel components, such as transportation fuels.

The esterification of carboxylic acids is an equilibrium reaction, where water drives the equilibrium to favor the free acids and excess alcohol of drives the esterification toward ester formation (see scheme 1 below).

Scheme 1

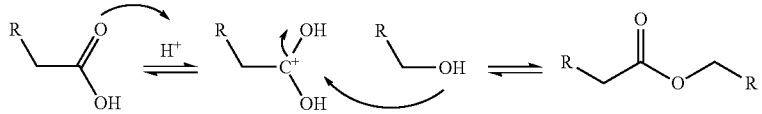

Aldehydes and ketones form acetals, where alcohol reacts with carbonyl carbon to form the acetal (see scheme 2 below).

Scheme 2

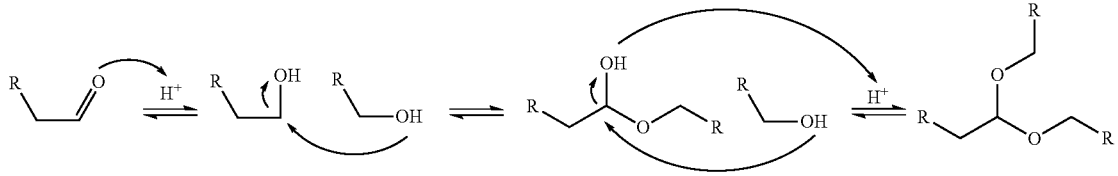

Acetals are more susceptible to hydrolysis than esters.

Bio-oils, particularly pyrolysis oils contain acids, aldehydes and ketones and typically from 15 to 30 wt % of water. Water prevents ester and acetal formation and increases hydrolysis of acetals. In the present invention water is removed efficiently using azeotropic distillation with at least one alcohol from bio-oil, particularly pyrolysis oil, whereby the formation and stability of esters and acetals is improved in the subsequent alcoholysis step.

FIG. 1 is a schematic diagram of a process in accordance with one embodiment of the invention. In this embodiment, in the first step feedstock comprising bio-oil 10 and alcohol 20 are fed to a reactor 100 wherein azeotropic distillation is carried out, yielding a gaseous component 30 and liquid component 40. Said gaseous component 30 comprises water and some alcohol and it is directed to separation unit 50 where water 60 is separated from the alcohol 70. The alcohol 70 originating from azeotropic distillation may be recycled to alcohol feed 20. The liquid component 40 comprising water-free bio-oil and alcohol is directed to alcoholysis reactor 200 where alcoholysis is carried out to yield alkoholysis product 80. Alcohol (free alcohol) 110 is separated from the alcoholysis product 80 in separation unit 150 and a converted bio-oil product 90 is obtained. The separated alcohol 110 may be recycled to alcohol feed 20.

If desired the azeotropic distillation and the alcoholysis may be carried out in the same reactor or in different reactors.

Suitably the volumetric ratio of the feedstock comprising bio-oil to alcohol is from 10:1 to 1:10. In the azeotropic distillation 1-6 volume, suitably 2-5 volume of the alcohol is distilled of and respectively alcohol is added to obtain the ratio in the range as defined above.

The amount of water removed in the azeotropic distillation may be monitored, and if desired said amount may be used for calculating the amount of added alcohol in the azeotropic distillation stage.

Any reactors, equipment, configuration and apparatus suitable for handling bio-oils may be used in the process and in the distillation step. As pyrolysis oil is corrosive, materials capable of resisting corrosion are suitable.

Suitably water is separated in the separation unit 50 with any suitable means, and according to one embodiment distillation may be used.

Free alcohol is separated from the alcoholysis product 80 in separation unit 150 using any suitable means, such as distillation, until the free alcohol content in the converted bio-oil product is in the range of 0-20% by weight, suitably 0-15%

In certain embodiments, the alcoholysis of the liquid component 40 may be carried out in any reactor type or configuration, including simple pipe reactors.

In certain embodiments of the process, the alcoholysis product may be further purified by one or more purification steps using a separator, said separation step optionally being carried out by filtration, extraction, decantation, centrifugation and any combinations thereof, said separator optionally being selected from the group consisting of a gas-liquid, liquid-liquid, three-phase, horizontal, vertical, tubular, rotary, turbine, and centrifugal separators, and any combinations thereof.

In one embodiment of the process, the azeotropic distillation of the feedstock comprising bio-oil oil with at least one alcohol is carried out at a temperature from 60 to 250° C., suitably from 65 to 230° C.

In one embodiment of the process, the azeotropic distillation of the feedstock comprising bio-oil oil with at least one alcohol is carried out under a pressure from 0.1 bar to normal atmospheric pressure (NTP).

In one embodiment of the process, the azeotropic distillation of the feedstock comprising bio-oil oil with at least one alcohol is carried out for 10 min to 20 h suitably from 0.5 to 8 h, particularly suitably from 0.5 to 3 h.

No catalysts are used in the azeotropic distillation step.

The liquid component 40 from the azeotropic distillation contains alcohol usually as volumetric ratio from 1:10 to 10:1 alcohol (v/v). According to one embodiment the volumetric ratio of the liquid component to alcohol is 0.05 to 10. In another embodiment of the current invention, the volumetric ratio is 0.25 to 1. In yet another embodiment of the current invention, the volumetric ratio is 0.25 to 0.5.

In one embodiment of the process, the liquid component 40 obtained from the azeotropic distillation is reacted with the alcohol or a mixture of alcohols contained in the liquid component, i.e. the alcoholysis is carried out, at a temperature between 60° C. and 450° C.

In one embodiment of the process, the liquid component 40 obtained from the azeotropic distillation is reacted with the alcohol or a mixture of alcohols contained in the liquid component, i.e. the alcoholysis is carried out under a pressure of between normal atmospheric pressure (NTP) and 250 bar, suitably from NTP to 150 bar.

The liquid component 40 obtained from the azeotropic distillation may be reacted with the alcohol or a mixture of alcohols for a length of time sufficient for the alcoholysis reaction to reach a desired level of completion. This will, in turn, depend on various factors including the temperature of the reaction, and the like.

In one embodiment, the reaction time of the alcoholysis step is between about 2 minutes and 1200 minutes. In another embodiment, the reaction time is between about 15 minutes and 120 minutes. In yet another embodiment, the reaction time is between about 30 minutes and 60 minutes. The reaction time depends on the temperature of the reactor. In higher temperatures the reaction time can be shortened.

The process may be carried out a batch process, semi-batch process or a continuous process. Any suitable apparatus or configuration known in the art may be used for said process.

An oily, liquid converted bio-oil product is obtained having less acidity, lower amount of acids, lower amount of oxygen containing compounds, decreased viscosity, and it is a less complicated mixture of compounds. It has clearly increased stability and it is less corrosive.

If desired the obtained converted bio-oil may be used as such, or it may be upgraded.

According to one embodiment of the invention, no additional catalyst is needed in the alcoholysis step, particularly if the bio-oil contains acids and/or acidic compounds. This is the case for example with pyrolysis oils, where acids are formed during pyrolysis. In this embodiment the esterification and acetalization reactions are autocatalytic with the acids contained in the feedstock and the reaction can be run to near completion (or to desired level) with excess of alcohol.

In another embodiment the alcoholysis maybe carried out in the presence of an alkoholysis catalyst, particularly in cases where the feedstock contains no acids. Said catalyst is suitably a solid catalyst. In one embodiment, the catalyst is selected from the group consisting of alumina, silica-alumina, hafnia, titania, and zirconia, and mixtures thereof.

The feedstock comprising bio-oil is selected from bio-oils and any fractions of bio-oils and any combinations thereof. Bio-oil means here any oils or oily components obtained from any known thermal processing of biomass, from any known hydrothermal processing of biomass, from any supercritical fluid treatment of biomass, from molten salt treatment of biomass and from ionic liquid treatment of biomass. Suitably pyrolysis oils and any combinations thereof are used. Said pyrolysis oil may be obtained from any pyrolysis process of biomass, including slow pyrolysis, fast pyrolysis, catalytic pyrolysis and hydropyrolysis (catalytic fast pyrolysis in the presence of hydrogen).

Biomass may typically comprise virgin and waste materials of plant, animal and/or fish origin or microbiological origin, such as virgin wood, wood residues, forest residues, waste, municipal waste, industrial waste or by-products, agricultural waste or by-products (including also dung or manure), residues or by-products of the wood-processing industry, waste or by-products of the food industry, solid or semi-solid organic residues of anaerobic or aerobic digestion, such as residues from bio-gas production from lignocellulosic and/or municipal waste material, residues from bio-ethanol production process, and any combinations thereof. Biomass may include the groups of the following four categories: wood and wood residues, including sawmill and paper mill discards, municipal paper waste, agricultural residues, including corn stover (stalks and straw) and sugarcane bagasse, and dedicated energy crops, which are mostly composed of tall, woody grasses.

Suitably biomass is selected from non-edible sources such as non-edible wastes and non-edible plant materials. Particularly suitably said biomass comprises waste and by-products of the wood-processing industry such as slash, urban wood waste, lumber waste, wood chips, wood waste, sawdust, straw, firewood, wood materials, paper, by-products of the papermaking or timber processes, where the biomass (plant biomass) is composed of cellulose and hemicellulose, and lignin.

The pyrolysis oil refers particularly to a complex mixture of oxygen containing compounds (oxygenates), comprising typically water, light volatiles and non-volatiles. Pyrolysis oil is acidic, with a pH of 1.5-3.8, and wood based pyrolysis oil typically has pH between 2 and 3. The exact composition of pyrolysis oil depends on the biomass source and processing conditions. Typically pyrolysis oil comprises 20-30% of water, 22-36% of suspended solids and pyrolitic lignin (including low molecular mass lignin and high molecular mass lignin), 8-12% of hydroxyacetaldehyde, 3-8% of levoglucosan, 4-8% of acetic acid, 3-6% of acetol, 1-2% of cellubiosan, 1-2% of glyoxal, 3-4% of formaldehyde, and 3-6% of formic acid by weight. Pyrolysis oil typically also comprises other ketones, aldehydes, alcohols, furans, pyranes, sugars, organic acids, lignin fragments, phenolics, extractives and small amounts of inorganics. The density of pyrolysis oil is approximately 1.2-1.3 kg/l and usually the water molecules which are split during pyrolysis stay bound within the complex pyrolysis liquid as an emulsion.

Optionally bio-oil fractions, suitably pyrolysis oil fractions may be used as feedstock or as part of it. Said fractions are suitably obtained by subjecting the bio-oil, particularly pyrolysis oil to one or more fractionation treatments.

Examples of alcohols suitable for the process can include aliphatic, aromatic, and alicyclic alcohols. In some embodiments, alcohols can include C1-C30 alcohols. In some embodiments, alcohols can include C1-C6 alkyl alcohols. In some embodiment, alcohols used herein can be mono-functional or multi-functional (e.g., one alcohol moiety or multiple alcohol moieties). Alcohols useful for the embodiments of the invention include but are not limited to methanol, ethanol, propanol, isopropyl alcohol, butanol, tetrahydrofurfuryl alcohol, ethylene glycol, propylene glycol, glycerol, benzyl alcohol, fatty alcohols, and any mixture thereof. Particularly suitable alcohols are C1-C6 primary and secondary alcohols.

Alcohols used with embodiments herein may also include those formed from biomass through fermentation processes. Therefore, alcohols used with embodiments herein may be derived from industrial processing wastes, food processing wastes, mill wastes, municipal/urban wastes, forestry products and forestry wastes, agricultural products and agricultural wastes, amongst other sources. In some embodiments, alcohols used herein can be formed from biological wastes using processes known as such.

Methanol is a side product from the pulp mill and it can be recovered from the concentration step of black liquor. This methanol can conveniently be used in the present invention.

In the process of the invention water can be driven out with azeotropic distillation with alcohol, followed by esterification and acetalization reactions. These reactions are autocatalytic reactions particularly in the presence of acids formed during pyrolysis and the reaction can be run to near completion (or to desired level) with excess of alcohol (methanol). Because water is removed, esterification of acids and formation of acetals from aldehydes and ketones by alcoholysis is enhanced. Acetals are more susceptible to hydrolysis than esters but they are more stable toward oxidation than aldehydes or ketones. Acetals are also able to decrease the self-condensation of aldehydes or ketones, known as aldol condensation. Aldol condensation is catalyzed by acids. Alcoholysis also lowers the concentration of carboxylic acids in bio-ils, such as pyrolysis oils, by forming their respective esters. Thus reduced acid number and acidity of the bio-oil (pyrolysis oil) improve the product storage stability too. Alcohols also react with reactive pyrolysis compounds, which lower their reactivity. For instance, reactive species such as furfurals, sugars, and aldehydes in general, easily react with alcohols forming ketals and other compounds. Aldehydes and related compounds are prone to polymerization and coking reactions. Lowering the concentration of these compounds and eliminating their reactivity improves the thermal stability of the resulting products, thereby increasing upgradability.

The alcohol separated from the azeotropic distillation step can be recycled back to the azeotropic distillation after removal of water and the excess alcohol (free alcohol) separated from the alcoholysis product can be recycled to the azeotropic phase without further purification.

With the process feedstocks comprising bio-oils, particularly pyrolysis oils can be upgraded in an effective and economic way, whereby the stability of the bio-oil is increased, amount of water is decreased, amount of acids and acid number are decreased, the bio-oil has reduced corrosion effect with respect to metals, the amount of oxygen is decreased and the burning properties are increased.

The converted bio-oil product may be used as such for heating purposes as heating oil, where it provides clear advantages, such as higher heating value and higher quality than that of conventional bio-oils, such as pyrolysis oils. Due the improved stability and quality it may also be used as starting material in wider range of processes including processes for producing fuels, fuel components, particularly transportation fuels, fine chemicals and chemical building-blocks for chemical production, and solvents.

If desired, the obtained converted bio-oil product may be subjected to any known hydroprocessing steps, and any pretreatment and purification steps. Particularly in hydroprocessing simple hydrogenation conditions are sufficient and no complicated measures are needed, the consumption of $H_2$ is lower due to lower $O_2$ content in the converted bio-oil product, the yields are increased and better control of products is achieved.

Further, the water content in the converted bio-oil product is significantly reduced, but the viscosity of the product is maintained in a range providing a freely flowing liquid.

The following examples are illustrative of embodiments of the present invention, as described above, and they are not meant to limit the invention in any way. The invention is illustrated also with reference to the drawings.

EXAMPLES

Example 1

Methanolysis of Pyrolysis Oil

Pyrolysis oil was freeze-dried to obtain dry pyrolysis oil, which was subjected to methanolysis in dry methanol. The freeze dried pyrolysis oil (10 g) was dissolved in 50 ml MeOH and refluxed at 65° C. for 7 hours. GC-MS and TAN (Total Acid Number) was measured after reaction. GC-MS (Gas Chromatograph-Mass Spectrometer) revealed methyl esters of acetic, propionic and butanoic acid and benzoic acids and acetals of furfural.

The GC-MS results of the pyrolysis oil and the product are provided in the following table 1. GC: Agilent 7890A, MSD: Agilent 5975C, Column: HP-1, 30 m, id 0.25 mm, film thickness 0.25 μm, Carrier gas: He

TABLE 1

| Retention time (min) | Identified structure | Retention time (min) | Methanolysis product |
|---|---|---|---|
| 3.334 | furfural | 5.147 | methoxy(furan-2-yl)methanol |
| 4.809 | 2,5-dimethyltetrahydrofuran | | |
| 8.515 | phenol | | |
| 11.721 | p-cresol | | |
| 12.556 | guaiacol (2-methoxyphenol) | | |
| 18.080 | 4-methylguaiacol | | |
| 19.424 | catechol | | |
| 24.082 | 4-methylcatechol | | |

TABLE 1-continued

| Retentiontime (min) | Identifiedstructure | Retentiontime (min) | Methanolysisproduct |
|---|---|---|---|
| 26.771 | (structure) | | |
| 27.730 | (structure) | 41.150 | (structure) |
| 31-33 | (structure) | | |

Example 2

Azeotropic Distillation of Pyrolysis Oil Followed by Methanolysis

Pyrolysis oil (45 g) was dissolved in 50 ml MeOH and heated to 65° C., when MeOH started to distill. When methanol distilled out fresh dry methanol (150 ml) was introduced to the pyrolysis oil. All together 150 ml of methanol was distilled from the pyrolysis oil. After distillation the distillation column was closed and pyrolysis oil was refluxed with methanol for 5 h. GC-MS and TAN was measured after the reaction. Pyrolysis oil (feedstock) had TAN (acid number) of 130. In the product it was reduced to 100. Water content was reduced from 30% to 5% measured by Karl-Fischer titration. GC-MS revealed methyl esters of acetic acid and benzoic acids and acetals of furfural.

The present invention has been described herein with reference to specific embodiments. It is, however clear to those skilled in the art that the process(es) may be varied within the bounds of the claims.

The invention claimed is:

1. A process for converting bio-oil, wherein said process comprises the steps, where a feedstock comprising bio-oil selected from bio-oils, any fractions of bio-oils and any combinations thereof is subjected to azeotropic distillation with at least one alcohol selected from C1-C30 alcohols and combinations thereof to yield a liquid component, and subjecting the liquid component to alcoholysis whereby converted bio-oil comprising esters and acetals is obtained.

2. The process according to claim 1, wherein the feedstock comprising bio-oils selected from oils or oily components obtained from thermal processing of biomass, from oils or oily components obtained from hydrothermal processing of biomass, from oils or oily components obtained from supercritical fluid treatment of biomass, from oils or oily components obtained from molten salt treatment of biomass, from oils or oily components obtained from ionic liquid treatment of biomass, and pyrolysis oils.

3. The process according to claim 1, wherein the alcohol is selected from C1-C6 primary and secondary alcohols.

4. The process according to claim 1, wherein the liquid component is subjected to alcoholysis, where said liquid component is reacted with the alcohol or a mixture of alcohols contained in the liquid component.

5. The process according to claim 1, wherein the azeotropic distillation is carried out at a temperature from 60 to 250° C.

6. The process according to claim 1, wherein the azeotropic distillation is carried out under a pressure from 0.1 bar to normal atmospheric pressure (NTP).

7. The process according to claim 1, wherein the alcoholysis is carried out at a temperature between 60° C. and 450° C.

8. The process according to claim 1, wherein in the alcoholysis is carried out under a pressure of between normal atmospheric pressure (NTP) and 250 bar.

9. The process according to claim 1, wherein a gaseous component is separated in the azeotropic distillation, alcohol is separated from the gaseous component and recycled to the azeotropic distillation.

10. The process according to claim 1, wherein from the alcoholysis step, an alcoholysis product is obtained and it is subjected to separation, where alcohol and converted bio-oil are obtained, and the alcohol is recycled to the azeotropic distillation.

11. The process according to claim 1, wherein the alcohol is methanol.

12. The process according to claim 2, wherein the alcohol is selected from C1-C6 primary and secondary alcohols.

13. The process according to claim 2, wherein the liquid component is subjected to alcoholysis, where said liquid component is reacted with the alcohol or a mixture of alcohols contained in the liquid component.

14. The process according to claim 3, wherein the liquid component is subjected to alcoholysis, where said liquid component is reacted with the alcohol or a mixture of alcohols contained in the liquid component.

15. The process according to claim 2, wherein the azeotropic distillation is carried out at a temperature from 60 to 250° C.

16. The process according to claim 3, wherein the azeotropic distillation is carried out at a temperature from 60 to 250° C.

17. The process according to claim 4, wherein the azeotropic distillation is carried out at a temperature from 60 to 250° C.

18. The process according to claim 2, wherein the azeotropic distillation is carried out under a pressure from 0.1 bar to normal atmospheric pressure (NTP).

19. The process according to claim 3, wherein the azeotropic distillation is carried out under a pressure from 0.1 bar to normal atmospheric pressure (NTP).

* * * * *